United States Patent [19]

Rock et al.

[11] Patent Number: 5,344,698

[45] Date of Patent: Sep. 6, 1994

[54] COMPOSITE UNDERGARMENT FABRIC

[75] Inventors: Moshe Rock, Andover; Douglas Lumb, Methuen, both of Mass.

[73] Assignee: Malden Mills Industries, Inc., Lawrence, Mass.

[21] Appl. No.: 981,321

[22] Filed: Nov. 24, 1992

[51] Int. Cl.$^5$ .................. B32B 7/00; D04B 1/00; A61M 5/00

[52] U.S. Cl. .................. 428/253; 428/913; 428/254; 604/371; 604/370; 604/374

[58] Field of Search ............... 428/131, 138, 152, 198, 428/186, 913, 378, 393, 394, 395, 253; 604/371, 375, 378, 382, 383, 394, 396

[56] References Cited

U.S. PATENT DOCUMENTS

| | | | |
|---|---|---|---|
| 3,613,687 | 10/1971 | Kennedy | 604/396 |
| 4,128,692 | 12/1978 | Reid | 428/398 |
| 4,195,634 | 4/1980 | DiSalvo et al. | 128/290 R |
| 4,212,301 | 7/1980 | Johnson | 128/285 |
| 4,244,367 | 1/1981 | Rollenhagen | 604/396 |
| 4,411,660 | 10/1983 | Dawn et al. | 604/396 |
| 4,560,381 | 12/1985 | Southwell | 604/396 |
| 4,589,877 | 5/1986 | Sivillich | 604/368 |
| 4,616,642 | 10/1986 | Martin et al. | 128/132 R |
| 4,639,254 | 1/1987 | LeGault et al. | 604/385 R |
| 4,650,479 | 3/1987 | Insley | 604/358 |
| 4,731,066 | 3/1988 | Korpman | 604/366 |
| 4,738,257 | 4/1988 | Meyer et al. | 128/156 |
| 4,813,950 | 3/1989 | Branch | 604/396 |
| 4,847,134 | 7/1989 | Fahrenkrug et al. | 428/186 |
| 4,938,753 | 7/1990 | Van Gompel et al. | 604/396 |
| 5,021,050 | 6/1991 | Iskra | 604/379 |
| 5,045,341 | 9/1991 | Shlenker | 427/2 |
| 5,074,854 | 12/1991 | Davis | 604/358 |
| 5,092,323 | 3/1992 | Riedel et al. | 604/305 |

Primary Examiner—George F. Lesmes
Assistant Examiner—Kathryne E. Shelborne
Attorney, Agent, or Firm—Gottlieb, Rackman & Reisman

[57] ABSTRACT

A composite textile fabric for moving moisture away from the skin is provided. The composite fabric includes a first fabric layer comprising either a polyester, acrylic or nylon material which has been rendered hydrophilic, a second fabric layer comprising at least 5% by weight of a super absorbent material and a barrier layer having a high moisture vapor transmission rate applied to said second fabric layer. The first fabric layer and the second fabric layer are formed integrally and concurrently by knitting a plaited construction.

18 Claims, No Drawings

COMPOSITE UNDERGARMENT FABRIC

BACKGROUND OF THE INVENTION

This invention relates to a composite undergarment textile fabric, and more particularly to a composite fabric comprising a hydrophilic polyester, acrylic or nylon layer, and an absorbent layer made of cotton, rayon, a super absorbent material or a blend thereof, with a breathable barrier layer applied thereto. Together, these layers act to move urine or other body fluids away from the skin and through an undergarment made with the composite fabric.

A significant problem for many elderly individuals is their inability to control urination, generally known as incontinence. Though many individuals with this problem are forced to wear an adult-size diaper, this can often be both degrading and because of its bulk, very uncomfortable. In addition, most adult sized diapers are not reusable. It would therefore be desirable to have an undergarment made of a material that looks, feels and can be laundered like conventional underwear, but which readily retains and transports urine away from the skin of the wearer.

Most conventional undergarment textile fabrics are likely to result in the substantial enclosure of urine between the wearer's skin and the undergarment. When saturation of the undergarment takes place, accumulated urine wets the body of the garment wearer such that he begins to feel uncomfortable.

Adult size diaper materials besides being bulky and uncomfortable, cannot be laundered or reused. Where a super absorbent material is used, that material is usually in the form of a powder. While commercially available super absorbent powders offer a range of water-absorbent characteristics, they can be difficult to incorporate into absorbent products. Furthermore, there is a tendency for them to migrate from their location. Special equipment is often required to handle them and they must be kept in place by gluing, fusing or lamination to a support structure. Also, the gels formed from powders and water have little integrity and are, therefore, difficult to contain within a structure when subject to pressure.

Accordingly, it would be desirable to provide a textile fabric which overcomes the above disadvantages, and which helps transport moisture such as urine away from the skin of the wearer.

SUMMARY OF THE INVENTION

Generally speaking, in accordance with the invention, a composite textile fabric for moving urine or other body fluids away from the skin and retaining it is provided. The composite fabric includes a first fabric layer comprised of synthetic yarn which is or has been rendered hydrophilic, and a second fabric layer that is comprised of a moisture absorbent yarn of which at least 5% by weight is a super absorbent fiber. The first fabric layer and the second fabric layer are formed integrally and concurrently by knitting a plaited construction so that the layers are distinct and separate yet integrated one with the other. Significantly, a barrier layer comprising a breathable material is deposited on the second fabric layer. The barrier layer provides a gating mechanism for promoting transport of urine from the first fabric layer as the water contained therein evaporates from the second fabric layer and through the barrier layer. The advantage of providing a breathable barrier layer is that the weight of liquid retained by the absorbent layer is slowly and continually reduced by evaporation without allowing liquid through the barrier layer to wet the outer garments of the wearer. The barrier layer may be monolithic and hydrophilic or microporous and hydrophobic or a combination thereof.

The first fabric layer is made from a polyester, acrylic or nylon material and is worn against the skin. Because the polyester, acrylic or nylon material of the first fabric layer is treated to be hydrophilic, urine from the skin is quickly transported through the first layer and is then absorbed by the second layer of the composite fabric. Water contained in the urine absorbed in the second fabric layer is then evaporated from the surface of the second layer and the water vapor is selectively transported through the barrier layer to the outside of the garment (the surface of the barrier layer).

Of significance is the fact that the fabric construction is plaited. This feature helps to create a substantial moisture concentration gradient between the surface of the polyester, acrylic or nylon layer (which transports urine from the skin), the absorbent layer (which absorbs the urine from the first layer), and the barrier layer (through which the water contained in the urine is evaporated).

Also of importance is the fact that a breathable barrier layer is deposed on the absorbent layer. Because the barrier layer has a high moisture vapor transmission rate, moisture retained by the absorbent layer evaporates without wetting the outer garment of the wearer.

Accordingly, it is an object of the invention to provide an improved composite textile fabric for enhancing the transport of body fluids, for example urine, away from the skin.

In addition, it is an object of the invention to provide an improved composite textile fabric having an outer breathable barrier layer which provides a gating mechanism for urine transport.

It is also an object of the invention to provide an improved composite textile fabric having a plurality of hydrophilic fibers for conducting liquid moisture.

Another object of the invention is to provide an improved composite textile fabric which includes plaited layers for promoting the moisture concentration gradient between the layers.

A further object of the invention is to provide a composite textile fabric which includes a super absorbent material.

Yet another object of the invention is to provide an improved textile fabric for an undergarment in which the undergarment has the drapeability and feel of a conventional undergarment and can be laundered and reused in a conventional manner.

Still another object of the invention is to provide a composite textile fabric which retains absorbed urine even when compressed.

Still other objects and advantages of the invention will in part be obvious and will in part be apparent from the following description.

The invention accordingly comprises the several steps and relation of one or more of the steps with respect to each of the others, and the material or materials having the features, properties, and relation of constituents which are exemplified in the following detailed disclosure, and the scope of the invention will be indicated in the claims.

DETAILED DESCRIPTION OF PREFERRED EMBODIMENT

The composite textile fabric of the invention includes a first fabric layer which has been rendered hydrophilic, and a second fabric layer comprising at least 5% by weight of a super absorbent material having a breathable barrier layer deposed on the second fabric layer. The first fabric layer and the second fabric layer are formed integrally and concurrently by knitting a plaited construction so that the layers are distinct and separate yet integrated one with the other.

The first fabric layer is made from a polyester, acrylic or nylon material and comprises between about 20% and 75% by weight of the composite fabric. The second fabric layer comprises between about 20 and 75% by weight of the composite fabric. The preferred material for the first fabric layer is polyester. The amount of each fabric layer is selected based on the desired weight of the composite fabric, the end use desired of the composite fabric and the requirements for transferring urine from the polyester, acrylic or nylon layer to the moisture absorbent layer, and from the moisture absorbent layer through the breathable barrier layer. The weight per unit area of the composite fabric is between about 3 ounces/yards$^2$ and 10 ounces/yard$^2$, depending upon the end use requirements for wetness control.

In accordance with the invention, the construction of the composite fabric is such that it is plaited -- although each fabric layer is distinct and separate, each is integrated with the other. As a result, the composite fabric functions as a single unit.

The composite fabric may be constructed as a warp or weft knit, such as a plaited jersey, interlock, plaited interlock, two-end fleece, three-end fleece, terry with regular plaiting, double terry, double needle raschel and tricot. The selection of fabric construction will be based on the need for certain enduse requirements such as thermal insulation, distancing the absorbent layer further away from the wearer's skin, or providing the thinnest possible underwear fabric. Where a raised surface fabric is desired, the terry or fleece construction, followed by surface finishing, would be selected.

The second layer, as stated above, must include in the yarn at least 5% by weight of a super absorbent fiber. Preferably, the second layer should include at least 25% by weight of a super absorbent fiber. The preferred moisture absorbent materials comprise a blend of cotton or rayon and a super absorbent fiber such as a copolymer of acrylic acid, the latter being partially neutralized. The use of a super absorbent fiber is desirable in that the fibers will absorb many times their own weight, even when under pressure and they will retain the absorbed liquid when subjected to pressure. They swell many times as they absorb fluids and they do it faster than powder due to the small diameter of the fibers, approximately 30 microns, which gives a very high surface area for contact with the liquid. Other benefits of fibers also derive from their physical form. Because they are long compared to their diameters (length to diameter ratio at least 100), they become entwined in a structure and are less liable to migrate through agitation. The fabrics containing fibers are flexible and soft even when high levels are added. These types of fibers are produced by: Toyobo Co. Ltd., Osaka, Japan; by Allied Colloids Limited, Bradford, England; and by Courtaulds Fibers Ltd., Coventry, England. The preferred fiber is LANSEAL F, produced by Toyobo Co. Ltd. Test results reveal that such fiber retains 40 to 60 times its weight in urine.

Alternatively, the second layer may be knit with a yarn that is comprised of cotton or rayon. If the second layer is knit with a yarn that is comprised of cotton or rayon, the second layer, itself, will be chemically modified after knitting the composite fabric by treatment with alkyl chlorides and cross linking of the resultant ethers to form carboxyl methylated cellulosic fibers, as is known to one of skill in the art, to render the layer super absorbent.

In a preferred embodiment, the second fabric layer includes cotton and super-absorbent fibers as the major constituents.

A breathable barrier layer is deposited on the second fabric layer. The barrier layer may be deposited by transfer coating from "release" paper. It may also be deposited by conventional film or membrane lamination techniques. The barrier layer is made of either a microporous hydrophobic material or a nonporous hydrophilic material.

The polyester, acrylic or nylon of the first layer is either round or modified cross-section, 0.3 to 6.0 denier, and either spun or filament. The layer is chemically modified or utilizes a modified fiber so that it is rendered hydrophilic, as described hereinbelow.

After constructing the composite fabric of the invention, the fabric may also be dyed as disclosed in co-pending U.S. Ser. No. 07/704,781, filed May 23, 1991, now U.S. Pat. No. 5,312,667. Also, an antimicrobial may be added to retard the growth of odor causing bacteria.

In order to render the polyester, acrylic or nylon layer hydrophilic, a low molecular weight polyester is added. The low molecular weight polyester is chosen from MILEASE T manufactured by I.C.I., SCOTCHRELEASE FC-226 manufactured by the 3-M Company of Minneapolis, Minnesota, ZELCON manufactured by DuPont of Wilmington, Delaware, and AVCONAV S.R. manufactured by AVCO of Tel Aviv, Israel.

The amount of the low molecular weight polyester added is between about 1.75 and 2.75 weight percent based on the weight of the composite fabric. The preferred amount is 2.25 weight percent based on the weight of the composite fabric.

One can also purchase polyester, acrylic or nylon yarn which is already hydrophilic. The surface of the yarn may be treated chemically during the spinning process. Alternatively, in manufacturing the yarn fibers, hydrophilic blocks such as polyethylene glycol are added during the polymerization process.

Examples include a chemically modified nylon such as HYDROFIL, a Nylon 6 copolymer manufactured by Allied Signal Inc. of Petersburg, Virginia; THERMASTAT, a modified polyester manufactured by DuPont of Wilmington, Delaware; and DUNOVA, a modified acrylic manufactured by Bayer of Leverkusen, Germany.

By using a chemically modified fiber or by chemically modifying the first fabric layer, the layer is rendered substantially hydrophilic. As a result, the transport of urine from the surface of the first fabric layer to the moisture absorbent layer is substantially enhanced. Particularly, urine is made readily transportable along the surface of each polyester, acrylic or nylon fiber.

A significant aspect of the inventive composite fabric is the deposition of a breathable barrier layer on the absorbent layer. The barrier layer comprises between about 3 and 20% by weight of the fabric. The barrier layer is adhered to the second layer by conventional membrane-film lamination or transfer coating technology. The barrier layer may be non-porous and hydrophilic or microporous and hydrophobic, prevents the wearer's outer garment from getting wet, and has a high moisture vapor transmission rate which enables the water contained in the urine retained by the second layer to evaporate and be transported away from the undergarment without wetting the outer garment of the wearer.

A second significant aspect of the inventive composite fabric is that there is nothing interposed between the first fabric layer and the urine absorbent layer. The two layers are formed integrally and concurrently by knitting a plaited construction so that the layers are distinct and separate yet integrated one to the other.

Together the layers act to move urine away from the skin and through an undergarment made with the composite fabric by the creation of a moisture concentration gradient. Evaporation into the exposed air from the second layer and through the barrier layer sets up the gradient which serves as the driving force to move or transport the moisture through the fabric.

In particular, urine is "transported" quickly through the first layer, and then absorbed by the second layer. In other words, the first layer acts as a buffer between the skin and the second layer, and as a result, the skin is maintained in a dry condition. The water contained in the urine is then evaporated and the vapor is transported through either the micropores of the hydrophobic barrier layer or the non-porous hydrophilic barrier layer.

A suitable microporous hydrophobic material is UCE 2000 manufactured by UCB Chemical Corp. of Drogenbos, Belgium; a suitable hydrophilic material is PORELLE manufactured by Provair of the United Kingdom.

For a more detailed discussion of suitable breathable barrier layer materials and their function, reference is made to co-pending U.S. Ser. No. 07/788,913 filed Nov. 7, 1991, now U.S. Pat. No. 5,204,156.

Optionally, another fabric layer may be laminated to the exposed portion of the barrier layer. This fabric layer may be jersey or a raised surface fabric.

The underwear textile fabric of the invention is drapeable with good stretch and recovery and can be cut and sewn to standard underwear sizes. It is similar in appearance to, and can be laundered as, normal underwear, but has absorbent properties similar to, and enhanced liquid retention properties compared with, those of bulky disposable diapers.

Although the fabric of this invention is preferably used as an underwear textile fabric, it may also be used for other purposes such as a bed pad for hospital or nursing facility.

It will thus be seen that the objects set forth above, and those made apparent from the preceding description, are efficiently attained, and since certain changes may be made in the product set forth above without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

We claim:

1. A composite textile fabric comprising a first fabric layer of a material selected from the group consisting of polyester, acrylic and nylon which has been rendered hydrophilic in order to quickly transport urine and other body fluids therethrough, a second fabric layer for absorbing said urine and other body fluids comprising at least 5% by weight of a super absorbent fiber, and a breathable barrier layer applied to the second fabric layer having a high moisture vapor transmission rate so that moisture retained by the second layer rapidly evaporates;

wherein the first fabric layer and the second fabric layer are formed integrally and concurrently by knitting a plaited construction.

2. The fabric of claim 1, wherein said second fabric layer has the barrier layer applied thereto by transfer coating.

3. The fabric layer of claim 1, wherein said barrier layer is applied to said second fabric layer by conventional film or membrane lamination techniques.

4. The fabric of claim 1, wherein said second fabric layer comprises at least 25% by weight of a super absorbent fiber.

5. The fabric of claim 1, wherein the second fabric layer comprises moisture absorbent materials selected from the group consisting of cotton, rayon and a super absorbent fiber.

6. The fabric of claim 5, wherein said moisture absorbent materials comprise a yarn blend of super absorbent fibers and at least one of cotton fibers and rayon fibers.

7. The fabric of claim 1, wherein said super absorbent material is a copolymer of partially neutralized acrylic acid.

8. The fabric of claim 1, wherein said fabric has a warp or weft knit construction selected from the group consisting of plaited jersey, interlock, plaited interlock, two-end fleece, three-end fleece, terry with regular plating, double terry, double needle raschel and tricot.

9. The fabric of claim 1, wherein the first fabric layer comprises between about 20% and 75% by weight of the fabric and said second fabric layer comprises between about 20 and 75% by weight of the fabric.

10. The fabric of claim 1, wherein said fabric has a weight per unit area of between about 3 ounces/yards$^2$ and 10 ounces/yards$^2$.

11. The fabric of claim 1, wherein said first fabric layer material includes a low molecular weight polyester in an amount between about 1.75 and 2.75 weight percent based on the weight of the composite fabric for rendering said material hydrophilic.

12. The fabric of claim 1, wherein the first fabric layer is made from a yarn that is rendered hydrophilic by chemically treating the surface thereof.

13. The fabric of claim 1, wherein the first fabric layer is made from a yarn which is rendered hydrophilic by adding hydrophilic blocks during polymerization.

14. The fabric of claim 1, wherein the barrier layer is selected from the group consisting of a microporous hydrophobic and a monolithic hydrophilic material or a blend thereof.

15. The fabric of claim 1, wherein the barrier layer comprises between about 3 and 20 weight percent of the fabric.

16. The fabric of claim 1, wherein said material of said first fabric layer is polyester.

17. The fabric of claim 1, wherein the second fabric layer is knit with a yarn which incorporates super absorbent fibers.

18. The fabric of claim 1, wherein said second fabric layer is chemically modified to render the layer super absorbent.

* * * * *